(12) United States Patent
Yamamura et al.

(10) Patent No.: US 9,408,948 B2
(45) Date of Patent: Aug. 9, 2016

(54) BIODEGRADABLE PARTICLES FOR MEDICAL TREATMENT AND VASCULAR EMBOLIZATION MATERIAL

(75) Inventors: Yasufumi Yamamura, Otsu (JP); Kazuhiro Tanahashi, Otsu (JP); Megumi Nakanishi, Otsu (JP); Masaki Fujita, Otsu (JP)

(73) Assignee: Toray Industries, Inc. (JP)

( * ) Notice: Subject to any disclaimer, the term of this patent is extended or adjusted under 35 U.S.C. 154(b) by 276 days.

(21) Appl. No.: 13/995,294

(22) PCT Filed: Dec. 19, 2011

(86) PCT No.: PCT/JP2011/079299
§ 371 (c)(1),
(2), (4) Date: Jun. 18, 2013

(87) PCT Pub. No.: WO2012/086569
PCT Pub. Date: Jun. 28, 2012

(65) Prior Publication Data
US 2013/0273372 A1    Oct. 17, 2013

(30) Foreign Application Priority Data

Dec. 20, 2010 (JP) .............................. 2010-282837

(51) Int. Cl.
| | |
|---|---|
| A61L 31/06 | (2006.01) |
| C08G 63/664 | (2006.01) |
| A61L 24/00 | (2006.01) |
| A61L 24/04 | (2006.01) |

(52) U.S. Cl.
CPC ............. *A61L 31/06* (2013.01); *A61L 24/0042* (2013.01); *A61L 24/046* (2013.01); *C08G 63/664* (2013.01); *A61L 2430/36* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 2002/0198332 | A1* | 12/2002 | Kasemura ............... | C08L 67/02 525/450 |
| 2009/0311337 | A1* | 12/2009 | Tanahashi et al. ........... | 424/497 |

FOREIGN PATENT DOCUMENTS

| | | |
|---|---|---|
| EP | 0 092 918 | 11/1983 |
| EP | 1 947 137 | 7/2008 |
| JP | 05-000969 A | 1/1993 |
| JP | 5-17245 | 3/1993 |
| JP | 2004-167229 A | 6/2004 |
| JP | 2005-312623 A | 11/2005 |
| JP | 2005-314535 A | 11/2005 |
| JP | 2007-145826 A | 6/2007 |
| JP | 2007-146146 A | 6/2007 |
| JP | 2007-291323 A | 11/2007 |
| JP | 2007-325910 A | 12/2007 |
| JP | 2009-525775 A | 7/2009 |
| WO | 97/15287 | 5/1997 |
| WO | 2009/129503 | 10/2009 |

OTHER PUBLICATIONS

Supplementary European Search Report dated Aug. 28, 2014 from corresponding European Patent Application No. 11 85 1593.
Katsumata, Kenji et al., "The toughening effect of a small amount of poly(ε-caprolactone) on the mechanical properties of the poly(3-hydroxybutyrate-co-3-hydroxyhexanoate)/PCL blend," *Polymer Journal*, Feb. 23, 2011, vol. 43, pp. 484-492.
Zhu, Zhiyong et al., "Rheological Characterization of Flow and Crystallization Behavior of Microbial Synthesized Poly(3-hydroxybutyrate-*co*-4-hydroxybutyrate)," *Macromolecules*, American Chemical Society, Jun. 7, 2003, vol. 36, pp. 4891-4897.

* cited by examiner

*Primary Examiner* — Alexandre Ferre
(74) *Attorney, Agent, or Firm* — DLA Piper LLP (US)

(57) ABSTRACT

Biodegradable particles for medical use and a vascular embolization material have improved flexibility, cause less aggregation among particles, and have improved particle shape-recovering ability after passing through a catheter or the like. The biodegradable particles for medical use are composed of an A1-B-A2 type triblock copolymer, wherein A1 and A2 are each a block of biodegradable copolymer constituted of monomers including glycolic acid, lactic acid and 6-hydroxycaproic acid, and B is a block of water-soluble polymer.

16 Claims, No Drawings

BIODEGRADABLE PARTICLES FOR MEDICAL TREATMENT AND VASCULAR EMBOLIZATION MATERIAL

TECHNICAL FIELD

This disclosure relates to biodegradable particles for medical use and a vascular embolization material.

BACKGROUND

As materials to embolize blood vessels and the like for the purposes of hemostasis upon incision of an affected area, blocking the nutrient supply to a tumor, maintenance of the concentration of an anticancer drug in a tumor, etc., polymer particles such as cross-linked acrylic particles, degradable starch particles, poly(lactic acid/glycolic acid) copolymers (JP 5-969 A) and block copolymers of polyethylene glycol and polylactic acid (JP 5-17245 B, JP 2004-167229 A, JP 2005-312623 A and JP 2007-291323 A) are widely used.

The above-mentioned polymer particles can be delivered through a microcatheter or the like to the target site for vascular embolization, but they have problems such as insufficient flexibility and occurrence of aggregation to cause clogging of the catheter, and irreversible deformation of the polymer particles themselves before they reach the target site.

To solve these problems, control of the elasticity of the polymer particles by blending a plurality of types of polymers (JP 2007-145826 A), improvement in the ability to pass through a catheter by covering the surfaces of polymer particles with polyethylene glycol (JP 2007-146146 A), use of chemically cross-linked polymer particles (JP 2005-314535 A) and the like have been reported, and improved technologies have been developed.

However, although improvement in the problems of controlling the elasticity of polymer particles and the ability to pass through a catheter can be seen in the improved technologies such as blending of a plurality of types of polymers (JP '826), covering of the surfaces of polymer particles (JP '146) and use of chemically cross-linked polymer particles (JP '535), improvement in the problem of irreversible deformation of polymer particles themselves is insufficient. Hence, further improvement has been demanded to attain good embolization of blood vessels and the like. That is, development of an embolization material for blood vessels and the like wherein the ability of the polymer particles to recover their original shape after passing through a catheter (hereinafter referred to as "particle shape-recovering ability") is enhanced has been demanded.

It could therefore be helpful to provide biodegradable particles for medical use and a vascular embolization material which have improved flexibility, cause less aggregation among particles, and have improved particle shape-recovering ability after passing through a catheter or the like.

SUMMARY

We thus provide the biodegradable particles and a vascular embolization material described in (1) to (11) below:

(1) Biodegradable particles for medical use composed of an A1-B-A2 type triblock copolymer, wherein:
   A1 and A2 are each a block of biodegradable copolymer constituted by monomers comprising glycolic acid, lactic acid and 6-hydroxycaproic acid, and
   B is a block of water-soluble polymer.
(2) The biodegradable particles for medical use according to (1) above, which have a compressive load of not more than 0.1 N and a compression recovery ratio of not less than 80% in the water-saturated state.
(3) The biodegradable particles for medical use according to (1) or (2) above, wherein in the block of biodegradable copolymer, the ratio of the structure originated from glycolic acid is 10 to 30%.
(4) The biodegradable particles for medical use according to any one of (1) to (3) above, wherein in the block of biodegradable copolymer, the ratio of the structure originated from lactic acid with respect to the structure originated from glycolic acid is not less than 50%.
(5) The biodegradable particles for medical use according to any one of (1) to (4) above, wherein in the block of biodegradable copolymer, the ratio of the structure originated from lactic acid is not more than 65%.
(6) The biodegradable particles for medical use according to any one of (1) to (5) above, wherein in the block of biodegradable copolymer, the ratio of the structure originated from 6-hydroxycaproic acid is 25 to 85%.
(7) The biodegradable particles for medical use according to any one of (1) to (6) above, wherein the weight-average molecular weight of said triblock copolymer is 3000 to 100000.
(8) The biodegradable particles for medical use according to any one of (1) to (7) above, wherein the weight-average molecular weight of the block of water-soluble polymer is 200 to 50000.
(9) The biodegradable particles for medical use according to any one of (1) to (8) above, wherein the water-soluble polymer is polyethylene glycol.
(10) The biodegradable particles for medical use according to any one of (1) to (9) above, whose average particle diameter is 20 to 2000 μm.
(11) The biodegradable particles for medical use according to any one of (1) to (10) above, whose particle diameter distribution is within the average particle diameter±100 μm.
(12) A vascular embolization material composed of the biodegradable particles for medical use according to any one of (1) to (11) above.

Since our biodegradable particles for medical use have improved flexibility, cause less aggregation among the particles, and can be easily delivered to the target site in a blood vessel or the like without causing clogging of the catheter, the particles can be used as an embolization material for blood vessels and the like. Further, since our biodegradable particles for medical use have improved particle shape-recovering ability after passing through a catheter or the like, the target site can be effectively embolized, and an embolization effect corresponding to the amount of the biodegradable particles for medical use used can be expected.

DETAILED DESCRIPTION

The terms used herein are as defined below unless otherwise specified.

Our biodegradable particles for medical use are characterized by being composed of an A1-B-A2 type triblock copolymer, wherein A1 and A2 are each a block of biodegradable copolymer constituted of monomers comprising glycolic acid, lactic acid and 6-hydroxycaproic acid, and B is a block of a water-soluble polymer.

The term "copolymer" refers to a copolymer constituted of two or more kinds of monomers. The term "block copolymer" refers to a copolymer in which two or more kinds of polymers which differ in their properties are covalently attached to each other or one another so that they form a molecular structure like a long chain, and the term "block" refers to each of "two or more kinds of polymers which differ in their properties." The term "triblock copolymer" refers to a block copolymer constituted by the blocks of A1, A2 and B, which are three kinds of polymers which differ in their properties. However, A1 and A2 are not necessarily different from each other, and may be the same polymers.

The term "A1-B-A2 type triblock copolymer" refers to a block copolymer in which an A1 block and an A2 block are covalently bound to the ends of a B block, respectively.

The phrase "biodegradable copolymer constituted of monomers comprising glycolic acid, lactic acid and 6-hydroxycaproic acid" refers to any biodegradable copolymer obtained by copolymerization of the three monomers of glycolic acid, lactic acid and 6-hydroxycaproic acid or by copolymerization of the three monomers with any other component(s). The term "biodegradable" refers to a property in which a copolymer is degraded, dissolved, adsorbed or metabolized in a living body or is excreted from inside to outside a living body.

The above-described three kinds of monomers of glycolic acid, lactic acid and 6-hydroxycaproic acid include any compounds which are to yield the same copolymers as those obtained when the three monomers are used. Examples of such compounds include glycolide, which is a cyclic dimer of glycolic acid; lactide, which is a cyclic dimer of lactic acid; and ε-caprolactam, which is a cyclic compound corresponding to 6-hydroxycaproic acid. That is, for example, of "the three kinds of monomers of glycolic acid, lactic acid and 6-hydroxycaproic acid," glycolic acid only may be replaced by glycolide, or all the three kinds of monomers may be replaced by glycolide, lactide and ε-caprolactam, respectively.

The above-mentioned any other component(s) include, for example, copolymers between hydroxycarboxylic acid(s) or derivative(s) thereof or diol(s) and dicarboxylic acid(s). Examples of "hydroxycarboxylic acid" include glyceric acid, hydroxybutyric acid, malic acid, tartaric acid, hydroxy valeric acid and 3-hydroxy hexanoic acid; examples of the diol include alkylene glycol such as ethylene glycol or propylene glycol; and examples of the dicarboxylic acid include oxalic acid, malonic acid, succinic acid, glutaric acid, adipic acid, pimelic acid, suberic acid, azelaic acid, sebacic acid or phthalic acid. Among these, as for those having an optical activity in the molecule such as malic acid, a D-isomer, an L-isomer or a mixture of D- and L-isomers thereof may be used.

The terms "the ratio of the structure originated from glycolic acid," "the ratio of the structure originated from lactic acid" and "the ratio of the structure originated from 6-hydroxycaproic acid" in the block of biodegradable copolymer in the A1-B-A2 type triblock copolymer refer to the ratio of glycolic acid, lactic acid and 6-hydroxycaproic acid, respectively, among all monomers which constitute the block of biodegradable copolymer.

If the above-mentioned ratio of the structure originated from glycolic acid in the block of biodegradable copolymer is too low, the biodegradability is not improved. On the other hand, if the ratio is too high, the solubility in an organic solvent decreases. Hence, molding of the obtained triblock copolymer becomes difficult. Thus, the ratio of the structure originated from glycolic acid in the block of biodegradable copolymer is preferably 10 to 30%, more preferably 12 to 28%.

If the ratio of the structure originated from lactic acid with respect to the structure originated from glycolic acid in "the block of biodegradable copolymer" is too low, the solubility in an organic solvent decreases. Hence, molding of the obtained triblock copolymer becomes difficult. Thus, the ratio of the structure originated from lactic acid with respect to the structure originated from glycolic acid in "the block of biodegradable copolymer" is preferably not less than 50%. On the other hand, if the ratio of the structure originated from lactic acid in "the block of biodegradable copolymer" is too high, the crystallinity is increased due to the structure originated from lactic acid. Hence, the biodegradability decreases. Thus, the ratio of the structure originated from lactic acid in "the block of biodegradable copolymer" is preferably not more than 65%, more preferably not more than 63%, still more preferably not more than 60%.

If the above-mentioned ratio of the structure originated from 6-hydroxycaproic acid in the block of biodegradable copolymer is too low, an appropriate particle shape-recovering ability cannot be given to the obtained biodegradable particles for medical use. On the other hand, if the ratio of the structure originated from 6-hydroxycaproic acid, which has a glass-transition point of as low as approximately −61° C., is too high, the glass-transition point of the obtained biodegradable particles for medical use decreases, and aggregation of the particles occurs at a temperature especially within a range of 10 to 40° C. Hence, the ratio of the structure originated from 6-hydroxycaproic acid in the block of biodegradable copolymer is preferably 25 to 85%, more preferably 27 to 80%.

"The ratio of the structure originated from glycolic acid," "the ratio of the structure originated from lactic acid with respect to the structure originated from glycolic acid," "the ratio of the structure originated from lactic acid" and "the ratio of the structure originated from 6-hydroxycaproic acid" in the block of biodegradable copolymer may be easily calculated from the results of measurement by the proton nuclear magnetic resonance spectroscopy (hereinafter referred to as "$^1$H-NMR"). For example, in cases where the block of biodegradable copolymer is constituted by three kinds of monomers of glycolic acid, lactic acid and 6-hydroxycaproic acid, the ratios may be calculated based on, respectively, the number of methylene groups in the structure originated from glycolic acid (chemical shift value: approximately 4.8 ppm), the number of methylene groups at the α-position in the structure originated from lactic acid (chemical shift value: approximately 5.2 ppm) and the number of methylene groups originated from the α-position of 6-hydroxycaproic acid (chemical shift value: approximately 2.3 ppm) which are grasped from the results of measurement by $^1$H-NMR.

Measurement Conditions
Apparatus: JNM-EX270 (manufactured by JEOL, 270 MHz)
Solvent: Deuterochloroform (containing 0.05 v/v % TMS as an internal standard)
Measurement Temperature: 20° C.

Examples of "water-soluble polymer" include polyethylene glycol (hereinafter referred to as "PEG"), PEG derivatives, block copolymers containing a block(s) of PEG and any other water-soluble polymers. Preferred are PEG, polypropylene glycol, polyvinyl alcohol, poly-acrylic acid, polyhydroxyethylacrylate, polyhydroxyethylmethacrylate and polyvinylpyrrolidone, and more preferred is PEG, in view of the fact that they are highly biocompatible.

If the weight-average molecular weight of the above-described biodegradable copolymer is too low, gelation of the obtained biodegradable particles occurs. Hence, the particles adhere to the inside of a catheter and so on. On the other hand, if the weight-average molecular weight is too high, the biodegradability of the obtained biodegradable particles decreases. Thus, the weight-average molecular weight of the above-described biodegradable copolymer is preferably 200 to 100000, more preferably 1000 to 80000. The weight-average molecular weights of the biodegradable copolymer described above and the water-soluble polymer described above are measured under the following measurement conditions by gel permeation chromatography (hereinafter referred to as "GPC method").

Measurement Conditions
    Column: TSKgel GMH$_{HR}$-M
        (7.8 mm Inner Diameter×30 cm Length, two in series; Tosoh Corporation)
    Eluent: Chloroform
    Column temperature: 35° C.
    Flow rate: 1.0 mL/minute
    Detection method: Refractive index
    Calibration curve: Prepared using polystyrene standard samples The weight average molecular weight of the triblock copolymer itself is preferably 3000 to 100000 to avoid an increase in the viscosity due to gelation of the triblock copolymer and to give appropriate degradability to the biodegradable particles for medical use. These weight average molecular weights are measured by the GPC method, similarly to the weight average molecular weight of the water-soluble polymer as described above.

Examples of the method of producing the above-described triblock copolymer include melt polymerization and ring-opening polymerization. Examples of the catalyst used in these polymerizations include tin halides such as tin chloride; organic acid tin salts such as tin 2-ethylhexanoate; diethyl zinc; zinc lactate; iron lactate, dimethylaluminum; calcium hydride; organic alkali metal compounds such as butyllithium and potassium t-butoxide; metal-porphyrin complexes; and metal alkoxides such as diethylaluminum methoxide.

The obtained triblock copolymer may be subjected to a granulation process without purification, or may be purified to remove unreacted substances, solvents and catalysts. As a method for such purification, for example, purification by fractional precipitation can be carried out. More specifically, a purified triblock copolymer can be obtained as a precipitate by dissolving the obtained triblock copolymer in a good solvent for the triblock copolymer and then adding the resulting solution dropwise to a poor solvent in a stirred state. Further, the purity of the triblock copolymer can be increased by heating the poor solvent to once dissolve the precipitate and then slowly cooling the resulting solution to allow production of the precipitate again. The term "good solvent" herein refers to an organic solvent in which not only the biodegradable polymer(s) which constitute(s) the blocks A1 and A2 but also the water-soluble polymer which constitutes the block B are dissolved. The term "poor solvent" herein refers to an organic solvent in which the biodegradable polymer(s) which constitute(s) the blocks A1 and A2 or the water-soluble polymer which constitutes the block B is not dissolved.

Examples of the good solvent used in the fractional precipitation include tetrahydrofuran, dichloromethane, chloroform, and mixed solvents thereof. The amount of the good solvent to be used varies depending on the amount of the raw materials fed and the composition of the triblock copolymer, and is preferably an amount with which the concentration of the triblock copolymer dissolved therein becomes 1 to 50 wt %, more preferably 1 to 25 wt %. Examples of the poor solvent include alcohol type organic solvents such as methanol and ethanol; ether type organic solvents such as dimethyl ether, ethyl methyl ether and diethyl ether; hydrocarbon type organic solvents such as pentane, hexane, heptane and octane; and mixed solvents thereof.

The compressive load of the biodegradable particles for medical use in the water-saturated state is preferably not more than 0.1 N, in view of obtaining a good ability to pass through a catheter thanks to an appropriate flexibility. The compression recovery ratio of the biodegradable particles for medical use in the water-saturated state is preferably not less than 80%, more preferably not less than 85%, still more preferably not less than 90%, in view of reducing the risk of flowing of the biodegradable particles further downstream of the target site in the blood vessel to be embolized.

"Compressive load" of the biodegradable particles for medical use is an indicator of the flexibility of the biodegradable particles for medical use, and refers to a load required for compressing a biodegradable particle for medical use so that the particle has a particle diameter of one-half (50%) of its original particle diameter. Resistance of the particles to passing through a catheter increases if the compressive load of the particles is large. For instance, the compressive load of Embosphere (registered trademark; Boston Scientific), existing vascular embolization particles, is 0.1 N.

The "compressive load" of the biodegradable particles for medical use may be measured with Single Column Testing System (type 3343; Instron) under the following conditions: diameter of the indenter, φ3 mm; load cell, 10N.

"Compression recovery ratio" of the biodegradable particles for medical use is an indicator of the particles' ability to recover their original spherical shape they have before compression when the particles are released from the compressed state such as after passing through a catheter, and refers to a ratio of the particle diameter after release from compression to the particle diameter before compression, which compression is performed by compressing the biodegradable particles for medical use so that they have a particle diameter of one-half (50%) of their original particle diameter.

The "compression recovery ratio" of the biodegradable particles for medical use may be calculated by taking pictures of the biodegradable particles for medical use with a microscope in the horizontal direction with respect to the direction of the compression during measurement of the compressive load described above, and then measuring the particle diameters before and after the compression.

The term "water-saturated state" refers to a state in which the water content of the biodegradable particles for medical use is constant when about 20 mg of the biodegradable particles for medical use are kept immersed in 10 mL of phosphate buffered saline at 37° C. (while rotating its container, a test tube, with a rotator at a rate of 0.5 rotation/second to shake the content of the test tube). The term "water content is constant" herein refers to a state in which, when the weight of the biodegradable particles for medical use immersed in phosphate buffered saline at 37° C. is measured every minute, the rate of weight change with time is within 10%. The "rate of weight change with time of the biodegradable particles for medical use" is a value calculated according to the Equation (1) below:

$$\text{Rate of weight change with time of the biodegradable particles for medical use (\%)} = \{W(t)-W(t-1)\}/W(t) \times 100 \quad (1)$$

W(t): Weight of the biodegradable particles for medical use after immersion in water for t minutes
W(t−1): Weight of the biodegradable particles for medical use after immersion in water for (t−1) minutes.

The average particle diameter of the biodegradable particles for medical use is preferably 20 to 2000 μm, more preferably 50 to 1500 μm in consideration of the diameter of the blood vessel as the target site for embolization. Further, it is preferred that the distribution width of the particle diameter be narrow, and the particle diameter is more preferably within the range of the average particle diameter±100 μm, still more preferably within the range of the average particle diameter±50 μm. The term "distribution width of the particle diameter" herein refers to the range of the particle diameter in which the diameters of not less than 99% of all particles are included. The particle diameter of the biodegradable particles for medical use can be measured by the light scattering method.

The shape of the biodegradable particles for medical use is preferably spherical at 37° C. since, in this case, the direction of the biodegradable particles for medical use hardly affects the condition of the embolus.

The biodegradable particles for medical use can be used to embolize a blood vessel. In such a case, the biodegradable particles for medical use may be used as they are, or may be dispersed in an appropriate dispersion medium or contrast medium before use.

Examples of the dispersion medium described above include vegetable oils such as sesame oil and corn oil; and distilled water for injection. The distilled water for injection may be supplemented with a dispersant(s) such as polyoxysorbitan fatty acid ester and/or carboxymethyl cellulose; preservative(s) such as methylparaben and/or propylparaben; isotonic agent(s) such as sodium chloride, mannitol and/or glucose; antiseptic(s), stabilizer(s), solubilizer(s) and/or vehicle(s) used for injections; and/or the like.

The contrast medium described above may be either ionic or nonionic, and examples of the contract medium include IOPAMIRON (registered trademark; Schering), HEXABRIX (registered trademark; Eiken Chemical Co., Ltd.), Omnipaque (registered trademark; Daiichi Sankyo Healthcare Co, Ltd.), Urografin (registered trademark; Schering), and IOMERON (registered trademark; Eisai Co., Ltd.).

EXAMPLES

Our particles and materials will now be described in detail by way of Examples, but this description is not limited to these.

Example 1

Into a flask, 6 g of PEG (SUNBRIGHT (registered trademark); average molecular weight: 20000; NOF Corporation), 3.6 g of glycolide (hereinafter "GA"), 7.2 g of L-lactide (Purac; hereinafter "LA") and 3.6 mL of ε-caprolactone (hereinafter "CL") were placed, and melt-mixed at 120° C. Thereafter, $12.0 \times 10^{-5}$ mol of tin dioctanoate (Wako Pure Chemicals) was added thereto, and the mixture was allowed to polymerize for 4 hours to obtain a crude triblock copolymer. The obtained crude triblock copolymer was dissolved in dichloromethane and then added dropwise to a large excess amount of diethyl ether to obtain white precipitates. The precipitates were washed with methanol and dried under reduced pressure, thereby obtaining a purified triblock copolymer.

Example 2

A triblock copolymer was obtained by the same method as in Example 1 except that the amounts of LA and CL were changed to 3.6 g and 10.1 mL, respectively.

Example 3

A triblock copolymer was obtained by the same method as in Example 1 except that the amounts of LA, CL and GA were changed to 1.0 g, 7.4 mL and 1.0 g, respectively.

Example 4

A triblock copolymer was obtained by the same method as in Example 1 except that the amounts of LA, CL and GA were changed to 1.0 g, 6.5 mL and 2.0 g, respectively.

Example 5

A triblock copolymer was obtained by the same method as in Example 1 except that the amounts of LA, CL and GA were changed to 6.0 g, 6.0 mL and 1.0 g, respectively.

Example 6

A triblock copolymer was obtained by the same method as in Example 1 except that the amounts of LA, CL and GA were changed to 1.0 g, 19.0 mL and 0.8 g, respectively.

Comparative Example 1

A triblock copolymer was obtained by the same method as in Example 1 except that LA and GA were not placed and that the amount of CL was changed to 16.7 mL.

Comparative Example 2

A triblock copolymer was obtained by the same method as in Example 1 except that CL and GA were not placed and that the amount of LA was changed to 18.0 g.

Comparative Example 3

A triblock copolymer was obtained by the same method as in Example 1 except that the amounts of LA and CL were changed to 6.0 g and 11.1 mL, respectively.

Comparative Example 4

A triblock copolymer was obtained by the same method as in Example 1 except that CL was not placed and that the amount of LA was changed to 14.4 g.

Comparative Example 5

A triblock copolymer was obtained by the same method as in Example 1 except that LA was not placed and that the amounts of CL and GA were changed to 20.9 mL and 7.5 g, respectively.

Comparative Example 6

A triblock copolymer was obtained by the same method as in Example 1 except that LA was not placed and that the amounts of CL and GA were changed to 22.2 mL and 6.0 g, respectively.

Comparative Example 7

A triblock copolymer was obtained by the same method as in Example 1 except that the amounts of LA, CL and GA were changed to 7.0 g, 4.0 mL and 2.0 g, respectively.

Comparative Example 8

A triblock copolymer was obtained by the same method as in Example 1 except that the amounts of LA, CL and GA were changed to 3.0 g, 8.0 mL and 6.0 g, respectively.

Evaluation of Solubility in Organic Solvent

The 30 mg aliquots of the triblock copolymers obtained in Examples 1 to 6 and Comparative Examples 1 to 6 were added to 1 mL of toluene, hexane, chloroform, dichloromethane, acetonitrile, tetrahydrofuran and acetone, and after stirring the mixtures, the presence of remaining insoluble matter or the turbidity of the solutions were visually checked. If a given triblock copolymer was dissolved in at least one of the above-described solvents without showing remaining insoluble matter nor being turbid, such a triblock copolymer was determined to be soluble in an organic solvent. The results of the evaluation of solubility in an organic solvent are shown in Table 1. The weight-average molecular weight (in the table referred to as "Average Molecular Weight" for short) of each triblock copolymer, and the ratio of the structure originated from GA (in the table referred to as "GA Ratio" for short), the ratio of the structure originated from LA (in the table referred to as "LA Ratio" for short) and the ratio of the structure originated from CL (in the table referred to as "CL Ratio" for short) in each triblock copolymer are also shown in Table 1. It should be noted that GPC method and measurement of $^1$H-NMR could not be carried out on the triblock copolymers obtained in Comparative Examples 5 and 6 because these copolymers were insoluble in an organic solvent. Hence, in Table 1, the weight-average molecular weight of these copolymers is not described, and the monomer feed ratio is described instead of the ratio of the structure originated from GA, etc.

Evaluation of Biodegradability

The triblock copolymers obtained in Examples 1 to 6 and Comparative Examples 1 to 6 were dissolved in dichloromethane to a concentration of 6 wt %, respectively. Each solution was poured into a glass mold with a height of 2 cm, a width of 2 cm and a depth of 5 mm, and the solvent was evaporated by heating it on a hot plate at 45° C. to obtain a triblock copolymer film. Each of the obtained triblock copolymer films was immersed in 10 mL of phosphate buffered saline, and subjected to rotary agitation in a thermostat bath at 37° C. If a given triblock copolymer film did not keep its film shape when observed 7 days after the start of the rotary agitation, such a triblock copolymer was determined to be biodegradable. The results of the evaluation of whether the triblock copolymer is biodegradable or not are shown in Table 1.

Preparation of Biodegradable Particles for Medical Use

The triblock copolymer obtained in Example 1 was dissolved in dichloromethane to a concentration of 7 wt %. Four hundred milliliters of aqueous solution was prepared by mixing 1 wt % polyvinyl alcohol and 40 wt % methanol, and using a syringe equipped with a 21G injection needle, 15 mL of the above-described triblock copolymer/dichloromethane solution was added dropwise thereto at a flow rate of 1.0 mL/min with stirring at 90 rpm at 5° C. The resulting mixture was stirred at 5° C., 100 rpm for 3 hours, and further stirred at room temperature, 250 rpm for 21 hours, and thereafter the 0/W solvent evaporation method was carried out to obtain spherical particles. Among the obtained spherical particles, those which passed through a sieve with a mesh size of 600 μm but could not pass through a sieve with a mesh size of 500 μm were collected, thereby obtaining spherical particles with an average particle diameter of 550 μm.

The same procedures were carried out on the triblock copolymers obtained in Examples 2 to 6 and Comparative Examples 1 to 4 to prepare biodegradable particles for medical use. The optimal conditions of the concentration of triblock copolymer/dichloromethane solution (in the table referred to as "Polymer Concentration" for short) and the concentration of methanol in an aqueous solution to which the above-mentioned polymer solution was added dropwise were sought to select from viewpoints of reducing the ratio of production of particles whose shape is not spherical and so on. The optimal conditions selected herein are shown in Table 2.

TABLE 2

| | Polymer Concentration [wt %] | Methanol Concentration [wt %] |
|---|---|---|
| Example 2 | 5 | 20 |
| Example 3 | 5 | 20 |
| Example 4 | 5 | 20 |
| Example 5 | 5 | 20 |
| Example 6 | 5 | 20 |
| Comparative Example 1 | 5 | 30 |
| Comparative Example 2 | 5 | 20 |
| Comparative Example 3 | 5 | 10 |

TABLE 1

| | Weight-Average Molecular Weight | GA Ratio [%] | LA Ratio [%] | CL Ratio [%] | Solubility | Biodegradability |
|---|---|---|---|---|---|---|
| Example 1 | 91427 | 24 | 49 | 27 | Soluble | Biodegradable |
| Example 2 | 56945 | 26 | 26 | 48 | Soluble | Biodegradable |
| Example 3 | 65312 | 13 | 11 | 76 | Soluble | Biodegradable |
| Example 4 | 52724 | 26 | 13 | 61 | Soluble | Biodegradable |
| Example 5 | 93365 | 11 | 60 | 29 | Soluble | Biodegradable |
| Example 6 | 61103 | 10 | 10 | 80 | Soluble | Biodegradable |
| Comparative Example 1 | 71678 | 0 | 0 | 100 | Soluble | Not biodegradable |
| Comparative Example 2 | 102511 | 0 | 100 | 0 | Soluble | Not biodegradable |
| Comparative Example 3 | 61772 | 0 | 46 | 54 | Soluble | Not biodegradable |
| Comparative Example 4 | 22434 | 21 | 79 | 0 | Soluble | Biodegradable |
| Comparative Example 5 | — | 33 | 0 | 67 | Not soluble | — |
| Comparative Example 6 | — | 25 | 0 | 75 | Not soluble | — |
| Comparative Example 7 | 87125 | 27 | 63 | 10 | Soluble | Biodegradable |
| Comparative Example 8 | — | 41 | 32 | 27 | Not soluble | — |

TABLE 2-continued

| | Polymer Concentration [wt %] | Methanol Concentration [wt %] |
|---|---|---|
| Comparative Example 4 | 5 | 10 |
| Comparative Example 7 | 5 | 10 |

Evaluation of Compressive Load and Compression Recovery Ratio

The compressive load and the compression recovery ratio of the biodegradable particles for medical use in the water-saturated state prepared from the triblock copolymers obtained in Examples 1 to 6 and Comparative Examples 1 to 4 were calculated. The results are shown in Table 3.

TABLE 3

| | Compressive Load [N] | Compression Recovery Ratio [%] |
|---|---|---|
| Example 1 | 0.062 | 95 |
| Example 2 | 0.042 | 90 |
| Example 3 | 0.095 | 93 |
| Example 4 | 0.083 | 98 |
| Example 5 | 0.068 | 94 |
| Example 6 | 0.096 | 95 |
| Comparative Example 1 | 1.4 | 98 |
| Comparative Example 2 | Collapse | — |
| Comparative Example 3 | 0.23 | 80 |
| Comparative Example 4 | Collapse | — |
| Comparative Example 7 | 0.150 | 72 |

Evaluation of Ability of Biodegradable Particles for Medical Use to Pass through Catheter Each of the 200 mg aliquots of the biodegradable particles for medical use obtained in Example 1 was dispersed in 2 mL of distilled water for injection. Each of these dispersions was injected from a syringe into a microcatheter (RENEGADE; Boston Scientific) having a total length of about 1500 mm and a tip inner diameter of 530 μm. As a result, it could be confirmed that the biodegradable particles for medical use could be smoothly injected into the microcatheter without showing adhesion to the syringe wall. After the injection of the dispersion, the microcatheter was cut along the longitudinal direction to visually observe its inner surface. As a result, no residual spherical biodegradable particle for medical use was found. The biodegradable particles for medical use before and after passing through the catheter were visually observed and compared to find that no deformation nor collapse of the particles was observed.

INDUSTRIAL APPLICABILITY

Our biodegradable particles for medical use can be used to embolize blood vessels in the medical field.

The invention claimed is:

1. Biodegradable particles for medical use composed of an A1-B-A2 type triblock copolymer, wherein:
    A1 is a block of biodegradable copolymer constituted of monomers comprising glycolic acid, lactic acid and 6-hydroxycaproic acid,
    A2 is a block of biodegradable copolymer constituted of monomers comprising glycolic acid, lactic acid and 6-hydroxycaproic acid,
    B is a block of water-soluble polymer, and
    a ratio of a structure originated from 6-hydroxycaproic acid in the blocks of biodegradable copolymer of A1 and A2 is 25 to 85%.

2. The biodegradable particles according to claim 1, which have a compressive load of not more than 0.1 N and a compression recovery ratio of not less than 80% in the water-saturated state.

3. The biodegradable particles according to claim 2, wherein in said block of biodegradable copolymer, the ratio of the structure originated from glycolic acid is 10 to 30%.

4. The biodegradable particles according to claim 2, wherein in said block of biodegradable copolymer, the ratio of the structure originated from lactic acid with respect to a structure originated from glycolic acid is not less than 50%.

5. The biodegradable particles according to claim 1, wherein in said block of biodegradable copolymer, the ratio of the structure originated from glycolic acid is 10 to 30%.

6. The biodegradable particles according to claim 5, wherein in said block of biodegradable copolymer, the ratio of the structure originated from lactic acid with respect to a structure originated from glycolic acid is not less than 50%.

7. The biodegradable particles according to claim 2, wherein in said block of biodegradable copolymer, the ratio of a structure originated from lactic acid is not more than 65%.

8. The biodegradable particles according to claim 5, wherein in said block of biodegradable copolymer, the ratio of a structure originated from lactic acid is not more than 65%.

9. The biodegradable particles according to claim 1, wherein weight-average molecular weight of said triblock copolymer is 3000 to 100000.

10. The biodegradable particles according to claim 1, wherein weight-average molecular weight of said block of water-soluble polymer is 200 to 50000.

11. The biodegradable particles according to claim 1, wherein said water-soluble polymer is polyethylene glycol.

12. The biodegradable particles according to claim 1, whose average particle diameter is 20 to 2000 μm.

13. The biodegradable particles according to claim 1, whose particle diameter distribution is within an average particle diameter±100 μm.

14. A vascular embolization material composed of the biodegradable particles for medical use according to claim 1.

15. Biodegradable particles for medical use composed of an A1-B-A2 type triblock copolymer, wherein:
    A1 is a block of biodegradable copolymer constituted of monomers comprising glycolic acid, lactic acid and 6-hydroxycaproic acid,
    A2 is a block of biodegradable copolymer constituted of monomers comprising glycolic acid, lactic acid and 6-hydroxycaproic acid,
    B is a block of water-soluble polymer,
    wherein in said blocks of biodegradable copolymer of A1 and A2, the ratio of a structure originated from lactic acid is not more than 65%, and
    wherein in said block of biodegradable copolymer, a ratio of a structure originated from lactic acid with respect to a structure originated from glycolic acid is not less than 50%.

16. Biodegradable particles for medical use composed of an A1-B-A2 type triblock copolymer, wherein:
    A1 is a block of biodegradable copolymer constituted of monomers comprising glycolic acid, lactic acid and 6-hydroxycaproic acid,
    A2 is a block of biodegradable copolymer constituted of monomers comprising glycolic acid, lactic acid and 6-hydroxycaproic acid, B is a block of water-soluble polymer,
wherein in said blocks of biodegradable copolymer of A1 and A2, the ratio of a structure originated from lactic acid is not more than 65%, and
a ratio of a structure originated from 6-hydroxycaproic acid in the block of biodegradable copolymer is 25 to 85%.

* * * * *